United States Patent [19]

Stakis

[11] Patent Number: 5,022,548
[45] Date of Patent: Jun. 11, 1991

[54] SEPARATION AND DISPOSAL OF MEDICAL AND DENTAL BIOLOGICAL WASTE

[76] Inventor: Anthony D. Stakis, 218 Hoodridge Dr., Pittsburgh, Pa. 15234

[21] Appl. No.: 470,227

[22] Filed: Jan. 25, 1990

[51] Int. Cl.⁵ ............................................. B65D 21/02
[52] U.S. Cl. .................................. 220/23.83; 220/404; 220/909; 206/501
[58] Field of Search .................. 220/1 T, 22, 23.83, 220/23.86, 23, 404, 4.27, 4.26, 554; 206/501, 506, 504, 508; 232/43.1

[56] References Cited

U.S. PATENT DOCUMENTS

| | | | |
|---|---|---|---|
| D. 265,125 | 6/1982 | Jordan | 232/43.1 |
| 823,433 | 6/1906 | Niswonger . | |
| 1,013,775 | 1/1912 | Hoffman | 220/1 T |
| 1,021,872 | 4/1912 | Kingsbury | 220/1 T |
| 1,141,727 | 6/1915 | Seaman . | |
| 3,201,035 | 8/1965 | Martin | 232/43.1 |
| 3,658,233 | 4/1972 | Voytko | 220/1 T |
| 3,825,150 | 7/1974 | Taylor . | |
| 3,995,924 | 12/1976 | Jones . | |
| 4,161,252 | 7/1979 | Howells | 206/508 |
| 4,331,074 | 5/1982 | Behman | 220/1 T |
| 4,577,778 | 3/1986 | Kim | 220/404 |
| 4,660,758 | 4/1987 | Tavel et al. . | |
| 4,715,572 | 12/1987 | Robbins | 220/404 |
| 4,750,639 | 6/1988 | Schearer . | |
| 4,823,955 | 4/1989 | Apps | 206/506 |
| 4,860,910 | 8/1989 | Zipper | 220/1 T |
| 4,893,722 | 1/1990 | Jones | 232/43.1 |

FOREIGN PATENT DOCUMENTS

| | | | |
|---|---|---|---|
| 0284059 | 9/1988 | European Pat. Off. | 220/909 |
| 3524781 | 1/1987 | Fed. Rep. of Germany | 220/909 |

*Primary Examiner*—Stephen Marcus
*Assistant Examiner*—S. Castellano

[57] ABSTRACT

A double receptacle is provided having two separate openings for disposing of biological and nonbiological waste in separate containers lined with readily removable plastic bags at least one of which is suitable for autoclaving. The unit comprises a base module, a center module, and a lid module, the center and lid each having openings for the bags. The lower plastic bag lines or fills the base module and has its opening in the center module; the upper plastic bag resides in the center module and access is provided from the lid module. The bags are held in place snugly at the nesting surfaces of the modules.

1 Claim, 1 Drawing Sheet

U.S. Patent
June 11, 1991
5,022,548
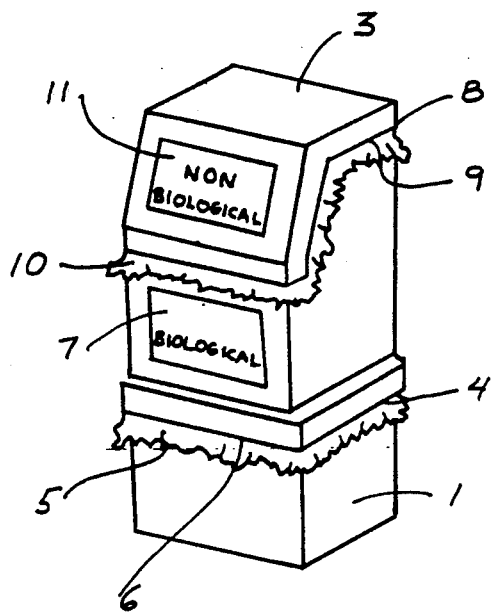
FIG 1
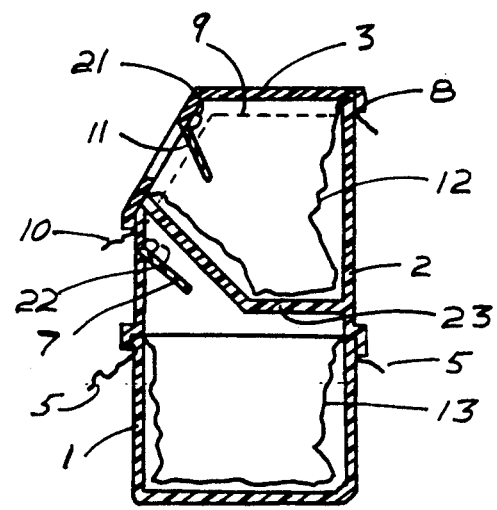
FIG 2
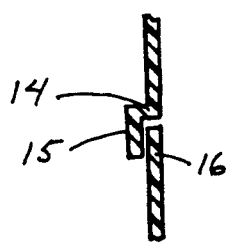
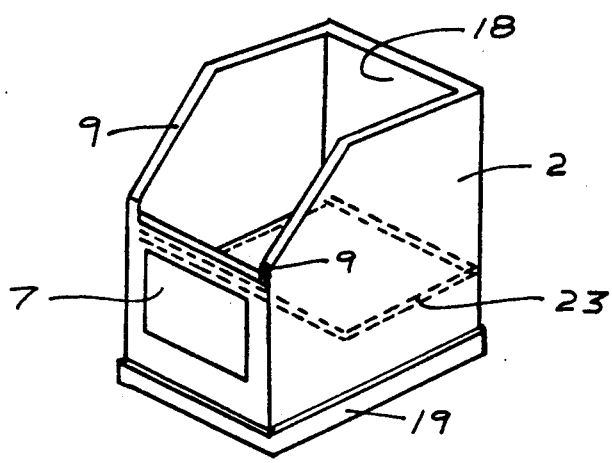

SEPARATION AND DISPOSAL OF MEDICAL AND DENTAL BIOLOGICAL WASTE

TECHNICAL FIELD

This invention relates to the collection and safe disposal of biological and other wastes such as are commonly generated in dentists' offices and physicians' offices. It provides a convenient receptacle small enough to be kept near the dentist chair or in a convenient place in the physician's examination room. The invention employs plastic bags which may be easily removed from the receptacle and closed at the same time to prevent spillage or other escape of the biological waste. The bottom of the upper bag is maintained at an intermediate level by a partition, preferably molded, on the bottom of the center module.

BACKGROUND OF THE INVENTION

Various kinds of receptacles have been used in the past to separate different kinds of articles while storing them for later use or disposal. An automatic clothes sorter, for example is described by Jones in U.S. Pat. No. 3,995,924; the sorter has four separate, removable bag compartments for different types of clothes. A construction is shown wherein the bags are suspended on a frame in a large hamper. In U.S. Pat. No. 4,660,758, Tavel et al show a combination separator-receptacle for recycling materials. It has four separate bin-like cavities which open outwardly by a pull handle causing the bins to swing out on a pivot. Schearer, in U.S. Pat. No. 4,750,639, discloses an arrangement for pre-sorting of household garbage—it consists primarily of a wire frame which supports three different plastic bags open at the top. While Jones shows a traditional clothes hamper lid, the Tavel et al and Shearer configurations are not satisfactory for saving biological waste for autoclaving, since they are open at the top. Jones's bags are also wide open at the top when one lifts the lid.

Niswonger, in U.S. Pat. No. 823,433, shows a laundry sorting receptacle having a plurality of different horizontal platforms which may be adjusted in position to approach a single exterior opening. Seaman, in U.S. Pat. No. 1,141,727, shows a button sorter which has three stacked bins, each having perforations in its lower surface so that when buttons are introduced to the top, the smaller ones will fall through to the middle or lower compartment where they may be removed through a separate access door provided. Neither Niswonger nor Seaman has bags or liners for his bins or compartments.

Taylor, in U.S. Pat. No. 3,825,150, shows a molded waste receptacle with resilient tabs on its upper edge for holding the tops of plastic bag inserts. Only one bag is used, however; in any event, the bag is retained in wide open position.

SUMMARY OF THE INVENTION

This invention relates to receptacles for medical and dental wastes and particularly to such receptacles of a convenient size which can be installed unobtrusively in a physician's or dentist's office and serve as a means for separating biological waste from other waste.

Good sanitary, hygiene and health practices, as well as, to some extent, regulatory authorities, require that biological waste be handled with care and common sense. Types of biological waste which may be generated or accumulated in a physician's or dentist's office are used bandages or the like removed from a patient, syringes, tongue depressors, compresses, various absorbents which may have been used in the mouth or on open wounds, extracted teeth, gloves, and so forth. Such materials which may have been in contact with an infected patient, or even removed from the patient himself or herself, containing blood and/or other bodily fluids or solid material, are to be sterilized as soon as possible and not merely discarded. Sterilization typically takes place in an autoclave which dentists and physicians generally will have available in their offices.

However, until now there has not been a convenient receptacle to guard properly against the possibility that the biological, possibly contaminated, material may be exposed to the air more than is necessary, i.e. for a period of perhaps an entire day or more before the health professionals are able to place the materials in an autoclave. The present invention provides an apparatus for temporarily storing biological waste prior to autoclaving in such a way as not to be mixed with ordinary or non-biological waste, and providing a storage bag unit which is easily separated from the receptacle, and readily placed in an office autoclave.

DETAILED DESCRIPTION OF THE INVENTION

The invention is most readily understood by referring to the drawings. In the drawings:

FIG. 1 is a perspective view of the complete unit,

FIG. 2 is a side sectional view of the assembled unit,

FIG. 3 is a detailed view of the preferred junction of the bottom of the center module and the upper portion of the base module, and FIG. 4 is a separate perspective view of the center module.

Referring now to FIG. 1, the invention is seen to have three major components—a base module 1, a center module 2, and a lid module 3. Center module 2 is inserted into the top edge 4 of base module 1 in a nesting manner illustrated more fully in FIG. 3. The periphery 5 of a plastic bag residing in base module 1 may be seen protruding from the interface 6 of base module 1 and center module 2. Center module 2 is provided with a generally rectangular door 7 preferably bearing the inscription BIOLOGICAL. As will be illustrated in FIG. 2, door 7 is spring-loaded so as to be normally closed; access through the door 7 enables the user to deposit biological waste through the periphery 5 of the bag residing in base module 1 without touching bag 12 since it is kept separate by partition 23. Lid module 3 rests on center module 2 in a manner similar to that of center module 2 resting on base module 1, i.e. its lower contour 8 conforms complementarily to the contour 9 of the upper edge of center module 2; the periphery 10 of plastic bag 12 protrudes from between contours 8 and 9. Bag 12 substantially fills the interior of center module 2, as will be further illustrated in FIG. 2. Lid module 3 is also fitted with a door 11, also spring-loaded in a normally closed position as is the door 7. Door 11 provides access to the open bag suspended in center module 2 while its periphery 10 is held in place by the snug fit of the lid module 3 onto the center module 2.

FIG. 2, a side sectional view of the assembled invention, shows the disposition of plastic bag 12 in the center module, suspended by its periphery 10 which is pinched between lid contour 8 and center module contour 9. The door 11 provides access only to bag 12 and is urged back to the closed position by spring 21. Door 7 is preferably located in the lower portion of center module 2 so that, as illustrated, ready access may be had to the interior of bag 13 without touching bag 12. Door 7 is also shown in the open position and is urged back to the closed position by spring 22. Bag 13 is suspended from the interface of center module 2 and base module 1 in the same manner as will be illustrated in FIG. 3.

FIG. 3 is a side sectional view of the interface of lid contour 8 and center module contour 9; it is also similar to the recommended nesting of base module 1 and center module 2, at interface 6, all as seen in FIG. 1. The configuration comprises a ledge 14 and a skirt 15 on the center module 2 and a complementarily shaped lip 16. Neither the ledge 14, the skirt 15 nor the lip 16 need be completely continuous—that is, they may consist of discontinuous portions so long as they are able to support the resting of the upper module on the lower one. They should fit snugly so they will retain bag 13 or bag 12.

FIG. 4 is presented to show the center module 2 as a separate portion of the invention in order more clearly to illustrate a preferred shape. It will be seen that the module 2 comprises a wall 18 which may be of a molded thermo-plastic such as ABS or a polyolefin. Skirt 19 is equivalent to skirt 15 in FIG. 3. Persons skilled in the art will recognize that the particular slanted contour between the lid module 3 and the center module 2 is not essential to the invention—it is recommended, however, as a way to provide ready access to door 11 on the lid module 3. Panel or partition 23 supports bag 12. It may be discontinuous but should have sufficient area to support bag 12.

Thus it will be seen that my invention comprises a stacked or nested, modular, unit in which the base is a hollow generally rectangular or cylindrical receptacle having an open-mouthed top dimensioned and configured to accommodate the open mouth of a plastic bag liner or insert, and having a peripheral skirt, flange or lip to accommodate snugly the lower profile of a center hollow module in a nesting or telescoping manner so the open mouth of the bag can be held in place by the fit of the center module; the center module has a spring-loaded access door near its lower edge to provide access to the open mouth of the bag in the base and also is shaped so that a second plastic bag or liner may be placed in the center module with its upper edge extending around the periphery of a skirt, flange or lip in the center module so that the third module of the unit, the lid, also having a spring-loaded access door, may be nested or telescoped on it to hold the upper bag in place.

The spring-loaded doors are preferably clearly marked so the user can clearly differentiate between the biological and non-biological waste. Whether or not the unit is to reside on a counter top, table, desk or the like, I prefer that the upper receptacle be labeled non-biological and the lower one biological. The purpose for this is to have the biological waste receptacle in the most convenient or accessible location. Spring-loaded doors assure that the open mouth of the plastic bag is not exposed to ambient air so that bacteria and possible noxious odors could escape. Clear markings will enable ordinary office cleaning crews to pick up only the non-biological waste on the top-most level. The possibility of confusing two similar bags as has been realized in the past is thus avoided.

If desired, the plastic bags may be of the self-sealing type so they may be sealed immediately on removal from the receptacle; in any event the biological container may be conveniently sealed with a clip or band immediately on removal from the container and placed as a whole in the autoclave. The plastic bag should be able to withstand the temperatures of an ordinary professional office autoclave. After autoclaving, the sealed bags may be stored for pickup by specialists in the disposal of biological waste.

What is claimed is:

1. A receptacle (for segregating biological and nonbiological wastes in a health profession office or the like) comprising (a) a base module container having an open top with a peripheral ledge for receiving a nesting center module container (b) a center module container having an open top with a peripheral ledge for receiving a nesting lid module, said center module container having a skirt of a size and shape adapted to rest on said peripheral ledge of said base module container and including a generally horizontal partition, said center module container having also a normally closed spring-loaded door providing access to a space below said partition and (c) a lid module having an open base of a size and shape adapted to rest on said peripheral ledge of said center module container and having also a normally closed spring-loaded access door, said base module container having a plastic bag therein retained in place at its top by said peripheral ledge of said base module container and said center module container nesting therein, and said center module container having a plastic bag therein retained in place at its top by said peripheral ledge of said center module container and said lid module container nesting therein.

* * * * *